United States Patent [19] [11] Patent Number: 5,310,954
Hiles et al. [45] Date of Patent: May 10, 1994

[54] PROCESS FOR PREPARING TETRAHYDROFURAN

[75] Inventors: Andrew G. Hiles, Pinner; Michael W. M. Tuck, London, both of England

[73] Assignee: Davy McKee (London) Limited, London, England

[21] Appl. No.: 828,903

[22] PCT Filed: Jul. 27, 1990

[86] PCT No.: PCT/GB90/01166

§ 371 Date: Jan. 31, 1992

§ 102(e) Date: Jan. 31, 1992

[87] PCT Pub. No.: WO91/01981

PCT Pub. Date: Feb. 21, 1991

[30] Foreign Application Priority Data

Aug. 4, 1989 [GB] United Kingdom ............. 8917864

[51] Int. Cl.$^5$ .................................... C07D 307/08
[52] U.S. Cl. .................................... 549/429
[58] Field of Search ............................ 549/429

[56] References Cited

U.S. PATENT DOCUMENTS

| 4,105,667 | 8/1978 | Thom | 260/299 |
| 4,175,009 | 11/1979 | Copelin | 203/96 |
| 4,665,205 | 5/1987 | Yamada et al. | 549/509 |
| 4,912,236 | 3/1990 | Palm et al. | 549/429 |

FOREIGN PATENT DOCUMENTS

| 143634 | 6/1985 | European Pat. Off. |
| 255400 | 2/1988 | European Pat. Off. |
| 2175894 | 6/1985 | United Kingdom |
| 2207429 | 2/1989 | United Kingdom |
| 2207431 | 2/1989 | United Kingdom |
| 8603189 | 6/1986 | World Int. Prop. O. |
| 8607358 | 12/1986 | World Int. Prop. O. |
| 8800937 | 2/1988 | World Int. Prop. O. |

OTHER PUBLICATIONS

Ind. Eng. Chem. Process Res. Dev., vol. 24, 1985, Samir I. Abu-Eishah et al.: "Design and Control of a Two-Column Azeotropic Distillation System", pp. 132–137.

"Distillation", Kirk Othmer Encyclopedia of Chemical Technology, vol. 7, pp. 869–870 (1979).

Primary Examiner—C. Warren Ivy
Assistant Examiner—Ba K. Trinh
Attorney, Agent, or Firm—Rothwell, Figg, Ernst & Kurz

[57] ABSTRACT

Separation of tetrahydrofuran (THF) from a mixture containing water, THF and a lower alkanol such as ethanol or methanol, is achieved by distillation in two zones, the vaporous mixture from the first zone being condensed and redistilled at a higher pressure in the second zone. Substantially pure THF is recovered from a lower part of the second zone, while the vapor from the top of the second zone is combined with the vapor from the first zone prior to condensation and the resulting condensate forms the liquid feed to the second zone. The process is suitable for recovering THF from complex reaction mixtures, containing also butane-1,4-diol and gamma-butyrolactone, obtained by hydrogenation of a dialkyl maleate.

5 Claims, 2 Drawing Sheets

PROCESS FOR PREPARING TETRAHYDROFURAN

FIELD OF THE INVENTION

This invention relates to a process for the recovery of tetrahydrofuran from mixtures containing tetrahydrofuran, one or more lower alkanols and water.

RELATED ART

A problem arises in attempting to recover pure tetrahydrofuran from a mixture that contains also water and a lower alkanol because tetrahydrofuran forms azeotropes with water and also with lower alkanols, such as methanol and ethanol.

Mixtures containing both a lower alkanol and water, in addition to tetrahydrofuran, are formed, for example, in the production of butane-1,4-diol and/or gammabutyrolactone by hydrogenation of a (di-$C_1$- to $C_4$-alkyl) maleate, fumarate, succinate, or a mixture of two or more thereof, according to the teachings of EP-A-0143634, WO-A-86/03189, and WO-A-86/07358. These mixtures contain, besides butane-1,4-diol and gamma-butyrolactone, varying amounts of tetrahydrofuran as well as water and a lower alkanol corresponding to the $C_1$- to $C_4$-alkyl moiety of the starting ester, such as ethanol. In addition such mixtures may contain a minor amount of dialkyl succinate and small amounts of "heavies", such as the corresponding $C_1$- to $C_4$-alkyl 4-hydroxybutyl succinate and other compounds, some of which have not been identified and hence can be classed as "unknowns".

Various processes have been described enabling substantially pure tetrahydrofuran to be recovered from such mixtures. One method of separating such mixtures is disclosed in GB-A-2175894. In this proposal it is stated:

"The crude product is fed to a first distillation column 5, which is operated under vacuum at a pressure of 0.27 bar with a head temperature of 48° C. The "light ends", i e. a mixture of tetrahydrofuran, ethanol, water, and n-butanol, are stripped off in column 5, recovered overhead in line 6, and passed to a second distillation column 7. Column 7 is operated at 1.2 bar at a head temperature of 58° C. A first tetrahydrofuran/water azeotrope is recovered overhead in line 8 and is passed to a third distillation column 9 which is operated at 7.0 bar with a head temperature of 126° C. Essentially pure tetrahydrofuran is recovered as a bottom product from third distillation column 9 in line 10. The overhead product in line 11 from third column 9 is a second tetrahydrofuran/water azeotrope which is markedly richer in water than the first tetrahydrofuran/water azeotrope from the second column 7. This second azeotrope is recycled from line 9 by way of line 6 to the second column 7"

Similar proposals appear in EP-A-0255400, and WO-A-88/00937.

Extractive distillation with butane-1,4-diol has been proposed in GB-A-2207429. Another proposal involving extractive distillation with butane-1,4-diol or another polyol is disclosed in GB-A-2207431.

Extractive distillation using water to separate one or more aliphatic alcohols selected from the group consisting of methanol, ethanol, iso-propanol and t-butanol from a tetrahydrofuran stream comprising tetrahydrofuran, one or more of said alcohols and optionally water is disclosed in U.S. Pat. No. 4,175,009.

In U.S. Pat. No. 4,105,667 a tetrahydrofuran/water stream in line 42 "is further purified in column 44 where water is separated as a bottom stream through line 45, and THF is withdrawn as an overhead stream through line 46."

DD-A-137188 describes recovery of tetrahydrofuran from technical mixtures, such as condensed vapours from polybutylene terephthalate manufacture, by a process which involves extractive distillation with an added solvent such as butane-1,4-diol.

Extractive distillation using, for example ethylene glycol, is used in the separation of methanol and ethanol in the process of SU-A-1025709.

DD-A-237056 describes a process for extractive distillation to separate a methanol/tetrahydrofuran azeotrope obtained in the course of preparation of polybutylene terephthalate, using as selective extraction medium dilute solutions of alkali metal or alkali earth metal hydroxides in polyhydric alcohols, such as glycols; ethylene glycol and butane-1,4-diol are proposed as suitable polyhydric alcohols.

JP-A-53/39427 teaches water removal from tetrahydrofuran without use of a third component. The method comprises distilling water-containing tetrahydrofuran under reduced pressure to give an azeotropic distillate which is then re-distilled under normal or elevated pressure to give pure tetrahydrofuran and an azeotropic distillate with a greater water content than the first azeotropic distillate, this second azeotropic distillate being condensed and recycled to the first distillation column.

Distillation under vacuum of a mixture of tetrahydrofuran and ethanol is described in JP-A-53/130654.

Production of tetrahydrofuran by dehydration of butane-1,4-diol followed by subjecting the reaction product to extractive distillation, while supplying butane-1,4-diol as an extraction solvent to the system, is described in U.S. Pat. No. 4,665,205.

In view of the difficulty of separating the products of hydrogenation of di-($C_1$- to $C_4$-alkyl) maleates and succinates, and in particular to recover pure tetrahydrofuran therefrom, there is a need in the art to provide more efficient processes for the recovery of tetrahydrofuran from such mixtures.

The present invention seeks to provide an improved process for recovery of tetrahydrofuran from reaction mixtures containing same, for example reaction mixtures obtained by hydrogenation of di-($C_1$- to $C_4$-alkyl) maleates, fumarates and/or succinates or mixtures thereof.

According to the present invention there is provided a process for separating tetrahydrofuran from a feed mixture containing water, lower alkanol and tetrahydrofuran which comprises distilling the mixture in a first distillation zone at a first pressure, recovering from an upper part of the distillation zone a first vaporous mixture comprising water, lower alkanol and tetrahydrofuran, subjecting the material from the first vaporous mixture to condensation conditions in a condensation zone, passing condensate from the condensation zone to a second distillation zone operated at a second pressure higher than the first pressure, recovering from an upper part of the second distillation zone a second vaporous mixture comprising water, lower alkanol and tetrahydrofuran, that has a lower concentration of tetrahydrofuran than the first vaporous mixture, and recovering from a lower part of the second distillation zone a stream comprising substantially pure tetraydrofuran, characterised in that the second vaporous mixture is combined with the first vaporous mixture prior to admission to the condensation zone.

By the term "lower alkanol" we mean an alkanol containing from 1 to 4 carbon atoms. Such alkanols include methanol, ethanol, n-propanol, iso-propanol, n-butanol and sec-butanol. The process of the invention is particularly suitable for use with feed mixtures containing ethanol and/or methanol.

The process thus envisages using a single condenser for both distillation zones. This provides a saving in capital costs in construction of the plant. No reflux stream is used in the second distillation column. An advantage of the process is that the heat capacity of the column reboiler for the first distillation column is significantly reduced, typically by at least about 40%, e.g. by about 50% or more, compared with an arrangement in which the second vaporous mixture is condensed and admixed with the feed mixture before re-admission to the first distillation column. This means that the operating costs are correspondingly reduced. In addition, as the reboiler is smaller, the capital costs are correspondingly reduced. A further advantage of the process of the invention is that it enables use of a first distillation column of smaller diameter than is required if the second vaporous mixture is condensed and is recycled to the first distillation column in liquid form. This also results in a corresponding reduction in capital costs.

The first distillation zone may be operated under normal, reduced or elevated pressure in the range of from about 0.1 bar to about 5 bar. It will normally be preferred to operate the first distillation zone at a pressure of not more than about 2 bar, e.g. at a pressure of about 1.1 bar. The overhead temperature in the first distillation zone will depend upon the composition of the feed mixture supplied to that zone and the nature of the lower alkanol present therein, as well as upon the prevailing operating pressure. It will typically lie in the range of from about 0° C. to about 160° C.

The second distillation column is operated at an elevated pressure, normally in excess of about 5 bar up to about 20 bar. Preferably the second distillation column is operated at a pressure of not more than about 10 bar, e.g. at about 7 bar. Again, the overhead temperature in the second distillation zone will depend upon the nature of the lower alkanol and the composition of the first vaporous mixture, as well as upon the operating pressure prevailing in the second distillation zone. Typically it will lie in the range of from about 115° C. to about 215° C.

The feed mixture to the first distillation column is typically a crude reaction mixture obtained by hydrogenation, preferably vapour phase hydrogenation, of a di-($C_1$- to $C_4$-alkyl) maleate, fumarate, succinate or a mixture of two or more thereof, using an ester hydrogenolysis catalyst such as a reduced copper chromite catalyst or a reduced promoted copper chromite catalyst (e.g. a reduced barium-promoted copper chromite catalyst). Further teaching regarding vapour phase hydrogenation of such a mixture can be obtained from EP-A-0143634, WO-A-86/03189 and from WO-A-86/07358. Such reaction mixtures contain a major molar amount each of butane-1,4-diol and of a $C_1$- to $C_4$-alkanol, variable amounts of gammabutyrolactone, and minor amounts of di-($C_1$- to $C_4$-alkyl) succinate, n-butanol, tetrahydrofuran, water and "heavies" such as the corresponding $C_1$- to $C_4$-alkyl 4-hydroxybutyl succinate and "unknowns".

Typically the reaction mixture contains:

| Component | Mole % |
| --- | --- |
| Butane-1,4-diol | 30–50 |
| $C_1$- to $C_4$- alkanol | 45–55 |
| gamma-butyrolactone | 10–35 |
| Di($C_1$- to $C_4$-alkyl) succinate | 0.5–2 |
| n-butanol | 0.5–4 |
| Tetrahydrofuran | 1–10 |
| Water | 5–10 |
| "Heavies" and "unknowns" | 1–2 |

In a preferred process the lower alkanol is ethanol. The process of the invention can also be used with feed mixtures that contain other lower alkanols, such as methanol.

In order that the invention may be clearly understood and readily carried into effect, a preferred process in accordance with the invention will now be described, by way of example only, with reference to the accompanying diagrammatic drawings in which:

DESCRIPTION OF PREFERRED EMBODIMENTS

It will be understood by those skilled in the art that, as the drawings are diagrammatic, further items of equipment such as condensers, heat exchanger, reflux drums, column reboilers, pumps, vacuum pumps, temperature sensors, pressure sensors, pressure relief valves, control valves, flow controllers, level controllers, holding tanks, storage tanks, and the like, would additionally be required in a commercial plant. The provision of such additional items of equipment forms no part of the present invention and is in accordance with conventional chemical engineering practice.

Figure 1:
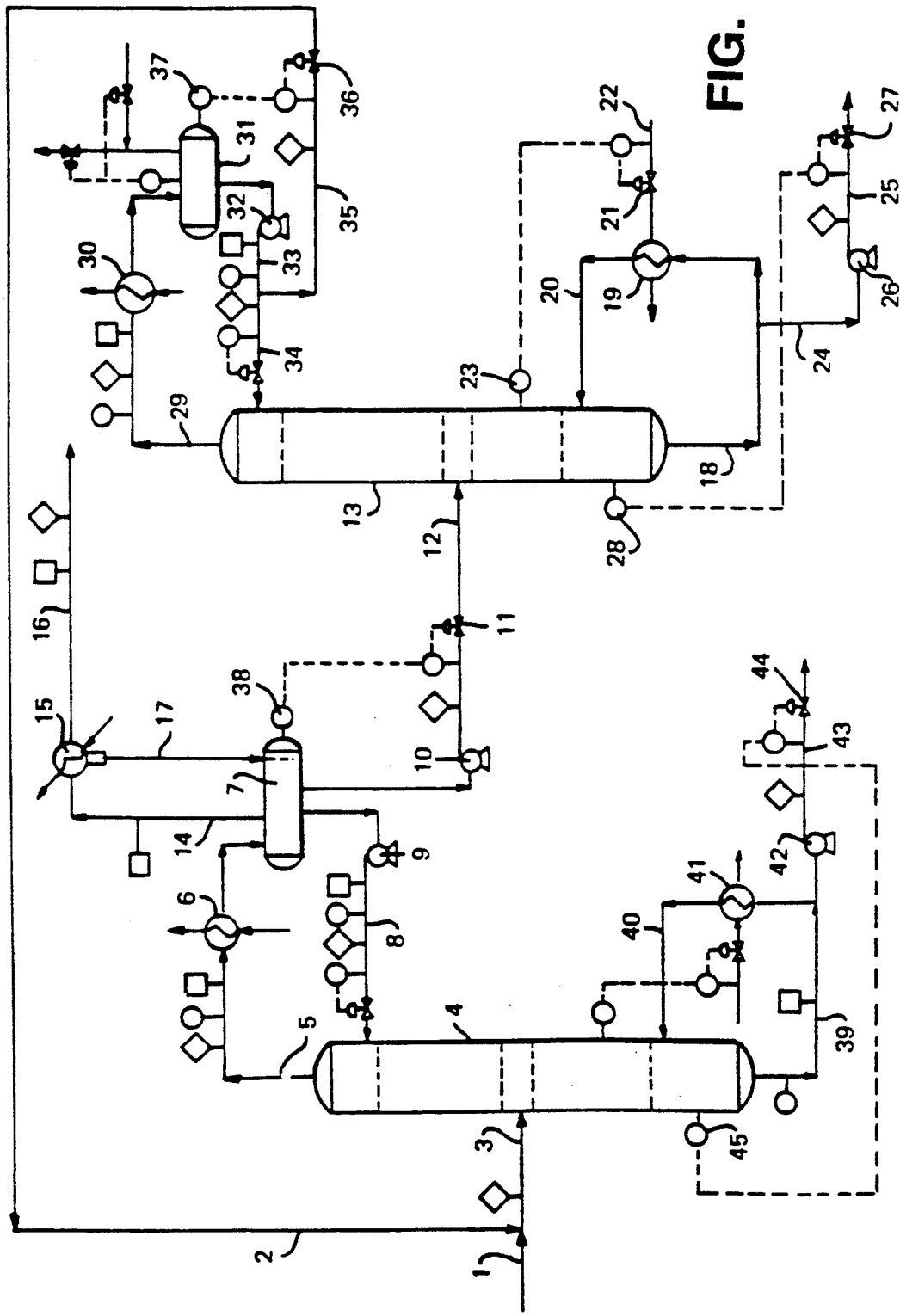
FIG. 1 is a flow diagram of a plant according to the prior art for the separation of tetrahydrofuran from a hydrogenation mixture produced by hydrogenation of diethyl maleate.

The comparative plant of FIG. 1 is designed according to similar principles to those outlined in the description of FIG. 1 of EP-A-0255400, for example, for separation of tetrahydrofuran from the hydrogenation mixture obtained upon vapour phase hydrogenation of diethyl maleate.

In the prior art plant of FIG. 1 the crude liquid hydrogenation mixture contains water, ethanol, n-butanol, tetrahydrofuran, gamma-butyrolactone, diethyl succinate, butane-1,4-diol and "heavies" including ethyl 4-hydroxybutyl succinate and "unknowns". The composition of this feed mixture will vary with time, in dependence upon the hydrogenation conditions selected for use during the hydrogenation of the diethyl maleate. Such conditions may alter over a period of time, for example as a result of ageing of the copper chromite catalyst. This feed mixture is supplied in line 1 and is admixed with a recycled liquid mixture of water, ethanol and tetrahydrofuran from line 2. The mixed feed flows on in line 3 to an appropriate intermediate tray of a first distillation column 4 which is operated at a pressure of 1.2 bar and with a head temperature of 58° C. A mixture of tetrahydrofuran, ethanol and water is recovered overhead in line 5 and is condensed in passage through the condenser 6. The resulting condensate is collected in drum 7. A large part of the condensate from drum 7 is recycled to the top of the first distillation column 4 to form a reflux stream in line 8 by means of pump 9. The remainder is pumped by pump 10 through valve 11 and line 12 to a second distillation column 13.

Reference numeral 14 indicates a vent line from drum 7 which is connected to a refrigerated condenser 15 from which line 16 leads to a vent stack (not shown). The condensate from refrigerated condenser 15 is returned to drum 7 by way of line 17.

Second distillation column 13 is operated at 7 bar with a head temperature of 126° C. Essentially pure tetrahydrofuran (typically at least about 99.9% pure tetrahydrofuran) is recovered from column 13 in line 18; part is recycled to the column through column reboiler 19 via line 20.

A valve 21 in steam line 22 controls the rate of supply of heat to column reboiler 19 under the control of a temperature controller 23. Product tetrahydrofuran is drawn off in line 24 and is pumped to storage in line 25 under the influence of pump 26. The flow of product tetrahydrofuran in line 25 is controlled by valve 27, which is in turn controlled by level controller 28 in the sump of second distillation column 13.

The overhead product in line 29 from column 13 is a mixture of water, ethanol and tetrahydrofuran. This mixture is condensed in condenser 30, the condensate being collected in drum 31. Part of the condensate is recycled by means of pump 32 via lines 33 and 34 to the top of column 13 to form a reflux stream, whilst the rest is recycled to first distillation column 4 through line 35 and pressure letdown valve 36 and line 2 under the control of level controller 37 in drum 31.

Reference numeral 38 indicates a level controller in drum 7 which controls valve 11 in line 12.

The bottom product mixture from column 4 in line 39 contains gamma-butyrolactone, diethyl succinate, butane-1,4-diol, and "heavies" and is essentially free from tetrahydrofuran; part is recycled in line 40 through column reboiler 41 whilst the remainder is withdrawn by means of pump 42 and passed to storage, prior to further distillation, in line 43 at a rate controlled by a valve 44 which is in turn under the control of level controller 45 in the sump of column 4.

At a feed rate of the mixture in line 1 of 7415 kg/hr, the design heat load of column reboiler 41 is 12.0 GBtu/hr (0.84 Gcal/sec), whilst the heat load on column reboiler 19 is 1.0 GBtu/hr (0.07 Gcal/sec). Typical flow rates in the various lines of the plant of FIG. 1 are summarised in Table 1 below.

TABLE 1

| Flow rate (kg/hr): | Line No. | | | | | | | | |
|---|---|---|---|---|---|---|---|---|---|
| | 1 | 2 | 5 | 8 | 12 | 29 | 25 | 34 | 43 |
| Water | 75 | 27 | 1158 | 1131 | 27 | 162 | — | 135 | 75 |
| Ethanol | 3677 | 7 | 301 | 294 | 7 | 40 | — | 33 | 3677 |
| n-butanol | 26 | — | — | — | — | — | — | — | 26 |
| THF | 311 | 182 | 21167 | 20674 | 493 | 1092 | 311 | 910 | 0 |
| GBL | 670 | — | — | — | — | — | — | — | 670 |
| DES | 362 | — | — | — | — | — | — | — | 362 |
| BDO | 2124 | — | — | — | — | — | — | — | 2124 |
| "Heavies" and "unknowns" | 70 | — | — | — | — | — | — | — | 70 |
| Total flow rate | 7415 | 216 | 22626 | 22099 | 527 | 1294 | 311 | 1078 | 7104 |

Notes:
THF = Tetrahydrofuran
GBL = gamma-butyrolactone
DES = Diethyl succinate
BDO = Butane-1,4-diol The plant of FIG. 1 is designed to extract, by distillation, solvent grade tetrahydrofuran product from a crude hydrogenation product stream which contains substantial quantities of ethanol (i.e. approximately 50 wt. % ethanol compared to typically 5 to 10 wt. % tetrahydrofuran) and small quantities of water. In practice the proportion of tetrahydrofuran in the stream in line 1 will vary with time, the concentration of tetrahydrofuran tending to increase as the hydrogenation catalyst ages and as the operating temperature of the hydrogenation zone has to be raised to compensate for loss of catalyst activity.

Design calculations show that as the concentration of tetrahydrofuran in the feed mixture in line 1 increases, the heat load on column reboiler 41 does not increase pro rata, while reduction of the tetrahydrofuran content of the feed mixture in line 1 does not result in a corresponding proportional reduction in the heat load on column reboiler 41 which remains substantially constant for a constant rate of supply of feed mixture in line 1.

As a result of such design calculations it was recognised that the determining duty of column 4 is not in achieving a vaporous mixture in line 5 with a high tetrahydrofuran concentration but rather in producing from the crude hydrogenation product stream supplied in line 1, which has a high ethanol/water ratio, a vaporous mixture in line 5 which has a high water/ethanol ratio. Hence the reason for the observed increase in heat load per tonne of tetrahydrofuran product on the column reboiler 41 was that, whilst the water content of the feed mixture in line 1 is roughly proportional to the tetrahydrofuran content thereof, the ethanol content remains essentially constant. This means that it becomes more difficult to obtain a high water/ethanol ratio in the overhead product in line 5 as the concentration of tetrahydrofuran in the feed mixture in line 1 is reduced. These factors result in a relatively high specific heat duty for the column reboiler 41.

Figure 2:
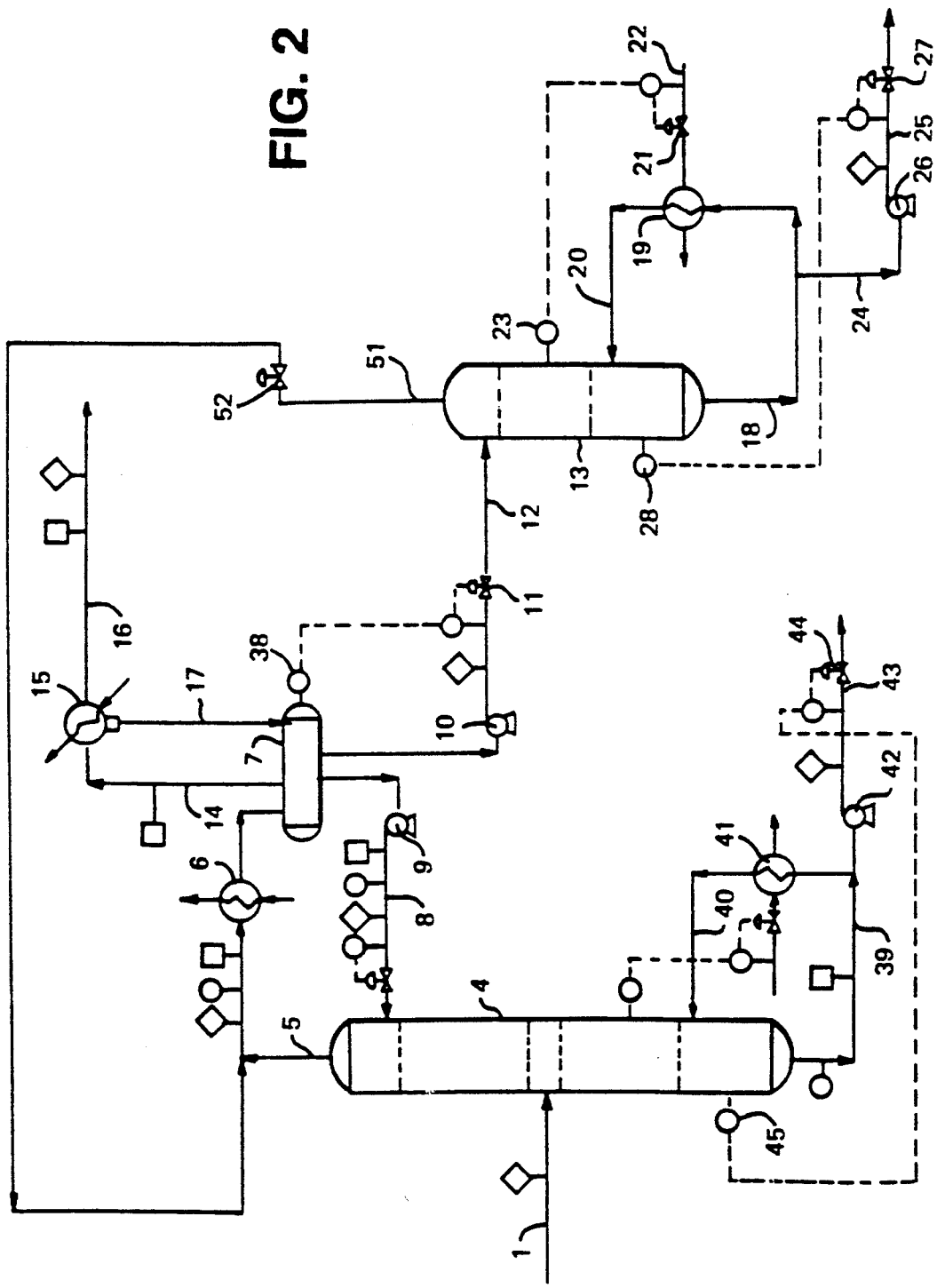
FIG. 2 is a flow diagram of a plant for a similar purpose constructed according to the teachings of the present invention.

The plant of FIG. 2 has many features in common with that of the plant of FIG. 1. Like reference numerals have accordingly been used to designate like parts in the two figures.

As will be seen from FIG. 2, the feed mixture in line 1 is fed directly into first distillation column 4. The major difference between the plant of FIG. 2 and that of FIG. 1 is that the overhead product from column 13 in line 51 is not condensed but is combined, after passage through a pressure letdown valve 52 with the vaporous stream in line 5 from the top of the first distillation column 4.

Typical flow rates in the plant of FIG. 2 are set out below in Table 2.

TABLE 2

| Flow rate (kg/hr): | Line No. | | | | | | |
|---|---|---|---|---|---|---|---|
| | 1 | 5 | 8 | 12 | 25 | 43 | 51 |
| Water | 71 | 543 | 543 | 55 | — | 71 | 55 |
| Ethanol | 3293 | 205 | 205 | 21 | — | 3293 | 21 |
| n-butanol | 17 | — | — | — | — | 17 | — |
| THF | 311 | 9803 | 9492 | 956 | 311 | 0 | 645 |
| GBL | 443 | — | — | — | — | 443 | — |
| DES | 626 | — | — | — | — | 626 | — |
| BDO | 2794 | — | — | — | — | 2794 | — |
| "Heavies" | 70 | — | — | — | — | 70 | — |
| Total flow rate | 7625 | 10551 | 10240 | 1032 | 311 | 7314 | 721 |

Notes:
THF = Tetrahydrofuran
GBL = gamma-butyrolactone
DES = Diethyl succinate
BDO = Butane-1,4-diol.

In the plant of FIG. 2 the operating temperatures and operating pressures used in columns 4 and 13 are essentially the same as those used in the plant of FIG. 1. The design heat capacity of the column reboiler 41 for the first distillation column 4 is 6.4 GBtu/hr (0.45 Gcal/sec) for the flow rates indicated in Table 2. The design heat capacity of the column reboiler 19 for the second distillation column 12 is then 0.6 GBtu/hr (0.04 Gcal/sec).

It will thus readily be seen that the design heat capacity of the column reboiler 19 for the second distillation column 13 is somewhat less in the case of the plant of FIG. 2 (0.6 GBtu/hr [0.04 Gcal/sec]) than in that of FIG. 1 (1.0 GBtu/hr [0.07 Gcal/sec]). Moreover the design heat capacity of the column reboiler 41 for the first distillation column is much lower for the plant of FIG. 2 (i.e. 6.4 GBtu/hr [0.45 Gcal/sec]) than the corresponding value for the plant of FIG. 1 (12.0 GBtu/hr [0.84 Gcal/sec]). Hence the overall heat input to the plant of FIG. 2 is approximately one half that of the heat input to the plant of FIG. 1 in order to produce the same volume of tetrahydrofuran per hour.

The invention is based upon the recognition that the composition of the vapour from the top of the second distillation column 13 has the same desirable high water/ethanol ratio as the overhead product in line 5 from the first distillation column 4. Hence it was realised that, if the recycle stream from the top of second distillation column 13 was fed to the top of the first distillation column 4, rather than being fed back into a zone of column 4 where the ethanol concentration is high, as for example by being combined with the high ethanol content crude hydrogenation product in line 1, then the duty on the column reboiler 41 of the first distillation column 4 could be substantially reduced in line with the rate of production of tetrahydrofuran, thereby yielding substantial operating cost savings. It was also realised that further cost savings in investment can be obtained by recycling the overhead product from the second distillation column 13 directly as a vapour, after passage through the pressure letdown valve 52, to the vapour recovery system from the top of the first distillation column 4. In addition it was recognised that, as the ethanol and water content of the overhead product from the second distillation column 13 in the plant of FIG. 1 is fixed by the quantity of ethanol and water in the feed stream to that column in line 12 and as the tetrahydrofuran/water azeotrope has a lower boiling point than the tetrahydrofuran/ethanol azeotrope, what happens in the rectification stage in the upper part of the column 13 in the plant of FIG. 1 is that the ethanol/water ratio increases towards the bottom of column 13, thus making production of pure tetrahydrofuran more difficult. In the plant of FIG. 2, however, column 13 can be made much smaller than in the plant of FIG. 1, since the top half of the distillation column 13 of FIG. 1 can be dispensed with, and no condensation system (e.g. the items 30, 31 and 32) is required. The reduction in size of the second distillation column 13 represents a significant capital cost saving. The necessary liquid flow to the second distillation column 13 is provided by using a higher recycle rate in line 51 in the plant of FIG. 2 than in line 2 of the plant of FIG. 1.

Compared with the plant of FIG. 1, the plant of FIG. 2 enjoys the following benefits:

1. The steam load for column reboiler 41 of the first distillation column 4 is reduced by approximately 50%;
2. The cross-sectional area of the first distillation column 4, its condensers 6 and 15, and its reboiler 41 are reduced in size by approximately 50% in line with the reduced heat load on column 4, resulting in corresponding capital cost savings;
3. The height of the second distillation column 13 is reduced by approximately 50% in comparison with the corresponding second distillation column 13 in the plant of FIG. 1;
4. No additional equipment, such as items 30, 31 and 32 of the plant of FIG. 1, is required in the plant of FIG. 2, since the recycle stream in line 51 is in vapour form; and
5. It is easier to maintain the quality of product tetrahydrofuran in line 25 since, by reducing the size and duty of second distillation column 13, there is less tendency for ethanol to reach lower levels of the column 13 and there is less risk of the tetrahydrofuran in line 25 being contaminated with ethanol.

Methanol, water and tetrahydrofuran also form a series of binary azeotropes one with another in a manner analogous to the behaviour of the ternary system, water-ethanol-tetrahydrofuran. If the feed mixture in line 1 is a reaction mixture obtained by hydrogenation of dimethyl maleate, then similarly good results are obtained with the plant of FIG. 2 to those described above. Similar operating processes can be used with correspondingly lower overhead temperatures in the two distillation columns in this case. As with a feed mixture which is a hydrogenation product mixture from hydrogenation of diethyl maleate, a product mixture from a plant for hydrogenation of dimethyl maleate can also vary with time due to changes in operating conditions adopted, for example, in response to ageing of the catalyst.

We claim:

1. In a process for separating tetrahydrofuran from a feed mixture containing water, lower alkanol and tetrahydrofuran which comprises distilling the mixture in a first distillation zone at a first distillation pressure which is in the range of from about 0.1 bar to about 5 bar, recovering from an upper part of the distillation zone a first vaporous mixture comprising water, lower alkanol and tetrahydrofuran, subjecting the material from the first vaporous mixture to condensation conditions in a condensation zone, passing condensate from the condensation zone to a second distillation zone operated at a second distillation pressure which is higher than the first distillation pressure and is in the range of from about 5 bar to about 20 bar, recovering from an upper part of the second distillation zone a second vaporous mixture comprising water, alkanol and tetrahydrofuran, that has a lower concentration of tetrahydrofuran than the first vaporous mixture, and recovering from a lower part of the second distillation zone a stream comprising substantially pure tetrahydrofuran, the improvement comprising combining the second vaporous mixture with the first vaporous mixture prior to admission to the condensation zone.

2. A process according to claim 1, wherein the lower alkanol is ethanol.

3. A process according to claim 1, wherein the lower alkanol is methanol.

4. A process according to claim 1, wherein the feed mixture to the first distillation zone is a crude reaction mixture obtained by hydrogenation of a di-($C_1$- to $C_4$-alkyl) maleate, fumarate, succinate or a mixture of two or more thereof.

5. A process according to claim 4, wherein the feed mixture contains
(a) from about 30 to about 50 mole % butane-1,4-diol;
(b) from about 45 to about 55 mole % lower alkanol;
(c) from about 10 to about 35 mole % gamma-butyrolactone;
(d) from about 0.5 to about 2 mole % di-($C_1$- to $C_4$-alkyl) succinate;
(e) from about 0.5 to about 4 mole % n-butanol;
(f) from about 1 to about 10 mole % tetrahydrofuran;
(g) from about 5 to about 10 mole % water; and
(h) from about 1 to about 2 mole % heavies and unknowns.

* * * * *

UNITED STATES PATENT AND TRADEMARK OFFICE
CERTIFICATE OF CORRECTION

PATENT NO. : 5,310,954

DATED : May 10, 1994

INVENTOR(S) : Andrew G. Hiles et al.

It is certified that error appears in the above-identified patent and that said Letters Patent is hereby corrected as shown below:

Col. 2, between lines 53 and 54, insert --SUMMARY OF THE INVENTION--.

Col. 3, line 3, "tetraydrofuran" should be --tetrahydrofuran--.

Signed and Sealed this

Sixth Day of September, 1994

Attest:

BRUCE LEHMAN

Attesting Officer

Commissioner of Patents and Trademarks